US00PP26361P2

(12) United States Plant Patent
Bernabe

(10) Patent No.: US PP26,361 P2
(45) Date of Patent: Jan. 26, 2016

(54) ***SALVIA* PLANT NAMED 'SALMON DANCE'**

(50) Latin Name: ***Salvia* hybrid**
Varietal Denomination: Salmon Dance

(71) Applicant: Catherine Bernabe, El Campello (ES)

(72) Inventor: Catherine Bernabe, El Campello (ES)

( * ) Notice: Subject to any disclaimer, the term of this patent is extended or adjusted under 35 U.S.C. 154(b) by 158 days.

(21) Appl. No.: 13/998,087

(22) Filed: Sep. 30, 2013

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

CNB New Plants Catalogue retrieved on May 14, 2015, retrieved from the Internet at <http://www.cnb.nl/EN/Pages/Product-Catalog.aspx?ProductId=177> one page.*
McHutchison Florexpo Unrooted Cuttings 2012-2013 retrieved on May 14, 2015, retrieved from the Internet at <http://mchutchison.com/McH_Florexpo_12-13.pdf> pp. 1-4, 29 and 98-100.*
New Plants and Flowers Jun. 1, 2012, retrieved on May 19, 2015, retrieved from the Internet at <http://www.newplantsandflowers.com/french-salvia-hybrids-on-dutch-trade-fair/> 2 pp.*

* cited by examiner

*Primary Examiner* — June Hwu
(74) *Attorney, Agent, or Firm* — Penny J. Aguirre

(57) ABSTRACT

A new cultivar of hybrid *Salvia*, 'Salmon Dance', that is characterized by its densely branched shrub-like plant habit, its large, fragrant flowers that are salmon pink in color, its floriferous flowering habit and its bright green leaves.

2 Drawing Sheets

Botanical classification: *Salvia* hybrid.
Variety denomination: 'Salmon Dance'.

BACKGROUND OF THE INVENTION

The present invention relates to a new and distinct cultivar of *Salvia* of hybrid origin and will be referred to hereafter by its cultivar name, 'Salmon Dance'. 'Salmon Dance' is an herbaceous perennial grown for landscape use.

The new *Salvia* resulted from a controlled breeding program conducted by the Inventor in Henansal, France. The Inventor made crosses in 2008 between unnamed proprietary plants of interspecific hybrid origin (*Salvia chamaedryoides*× *Salvia lycoides*) in the Inventor's breeding program as both the female and male parents. The characteristics of the parents are unknown as seeds where pooled and sown from several crosses. 'Salmon Dance' was selected as a single unique plant in 2008 from the resulting seedlings of the above crosses.

Asexual propagation of the new cultivar was first accomplished by the Inventor by vegetative stem cuttings in 2009 in Henansal, France. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Salmon Dance" as a unique cultivar of *Salvia*.

1. 'Salmon Dance' exhibits a densely branched shrub-like plant habit.

2. 'Salmon Dance' exhibits large, fragrant flowers that are salmon pink in color.
3. 'Salmon Dance' exhibits a floriferous flowering habit.
4. 'Salmon Dance' exhibits bright green leaves.

'Salmon Dance' can be most closely compared to the *Salvia greggii* cultivar 'Peach' (not patented) and typical plants of the species *Salvia microphylla*. 'Peach' differs from 'Salmon Dance' in being much less vigorous, in having smaller flowers, and in having a less dense and less shrub-like plant habit. Typical plants of *Salvia microphylla* are similar to 'Salmon Dance' in growth rate and plant habit. Typical plants of '*Salvia microphylla*' differ from 'Salmon Dance' in having smaller flowers and in being less floriferous.

BRIEF DESCRIPTION OF THE DRAWING

The accompanying colored photographs illustrate the overall appearance and distinct characteristics of a one year-old plant of the new *Salvia* as grown in a greenhouse in a 15-cm container in Henansal, France.

The photograph in FIG. 1 provides a view of 'Salmon Dance" in bloom.

Figure 1:
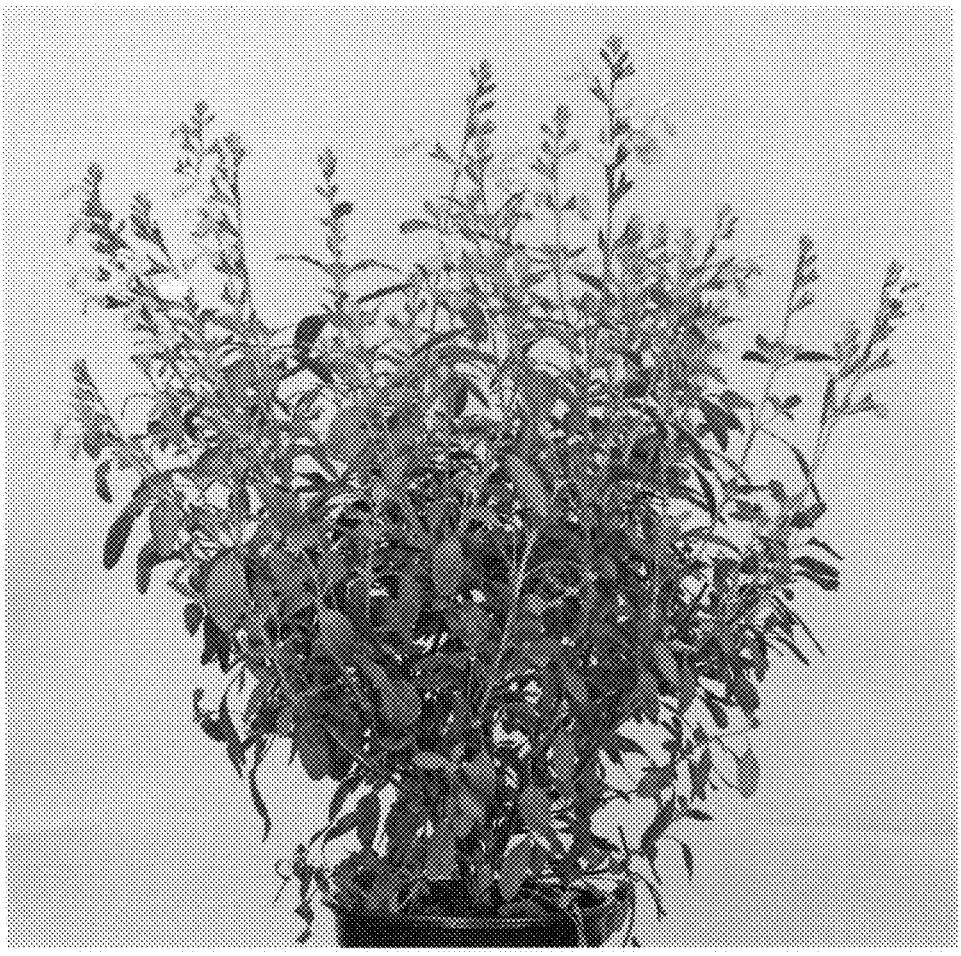
Figure 2:
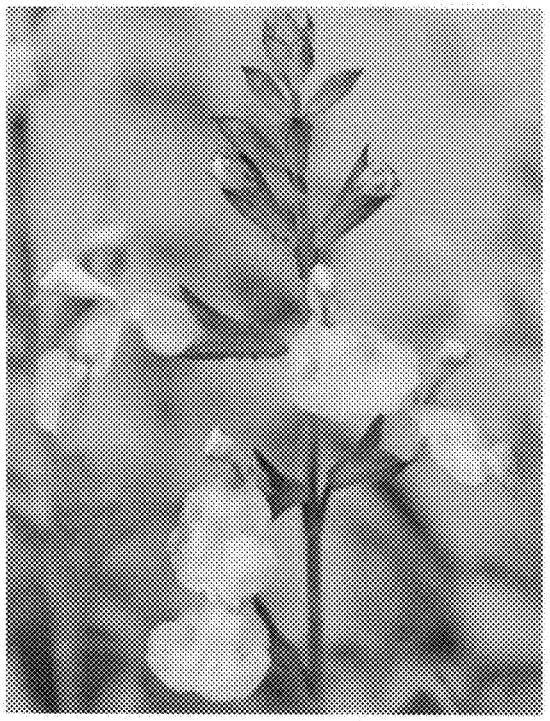

The photograph in FIG. 2 provides a close-up view of an inflorescence of 'Salmon Dance'.

Figure 3:
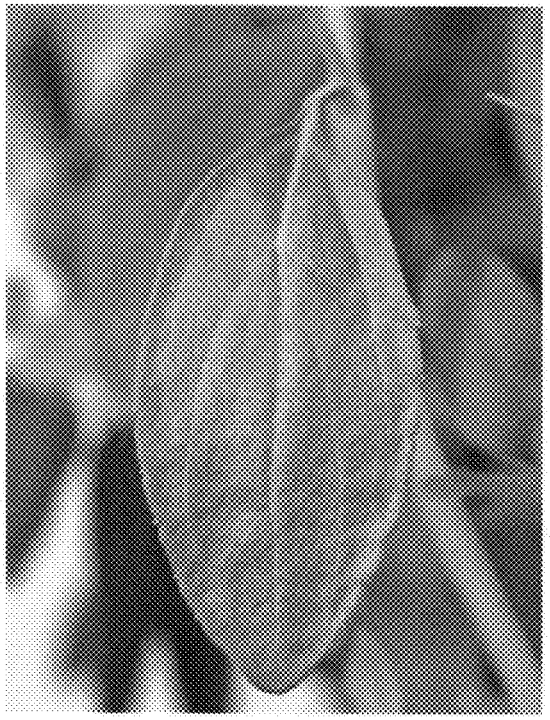

The photograph in FIG. 3 provides of close-up view of a leaf of 'Salmon Dance'.

The colors in the photographs may differ slightly from the color values cited in the detailed botanical description, which accurately describe the colors of the new *Salvia*.

DETAILED BOTANICAL DESCRIPTION

The following is a detailed description of one year-old plants of 'Salmon Dance' as grown in a greenhouse in 15-cm containers outdoors in Henansal, France. Plants were grown under average day temperatures ranging from 14° to 30° C. and average night temperatures of 8° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—May to first frost in Henansal, France.

*Plant type.*—Herbaceous perennial.

*Plant habit.*—Broad upright, densely branched and shrub-like.

*Plant size.*—Reaches up to 70 cm in height and 80 cm in spread.

*Cold hardiness.*—At least to U.S.D.A. Zone 8.

*Diseases and pests.*—No susceptibility or resistance to diseases or pests have been observed.

*Root description.*—Fibrous, non-spreading.

*Propagation*—Vegetative stem cuttings.

*Growth rate.*—Vigorous.

Stem description:

*Shape.*—Quadrangular.

*Stem color.*—137C.

*Stem size.*—Average of 13.6 cm in length and 2 mm in diameter.

*Stem strength.*—Strong.

*Stem aspect.*—Upright.

*Stem surface.*—Slightly glossy and densely covered with very short soft hairs; an average of 0.2 mm in length and 156D in color.

*Stem fragrance.*—When rubbed the leaves give a "sage" like fragrance.

*Internode length.*—Average of 2.7 cm.

*Branching.*—Average of 10 main stems, an average of 4 lateral braches per main stem.

Foliage description:

*Leaf shape.*—Ovate to elliptic.

*Leaf division.*—Simple.

*Leaf base.*—Short attenuate.

*Leaf apex.*—Obtuse.

*Leaf fragrance.*—When rubbed the leaves give a "sage" like fragrance.

*Leaf venation.*—Pinnate, upper surface is 138A in color, lower surface is 144B in color.

*Leaf margins.*—Crenate.

*Leaf arrangement.*—Opposite.

*Leaf attachment.*—Petiolate.

*Leaf surface.*—Very slightly rugose, glabrous, and dull on both surfaces.

*Leaf size.*—Up to 3 cm in length and 1.6 cm in width.

*Leaf color.*—Young leaves; upper and lower surface 143A, mature leaves; upper surface a blend of 137A and N137B, lower surface is N138B.

*Leaf quantity.*—Average of 10 (5 pairs).

*Petioles.*—Up to 1.3 cm in length and 1 mm in diameter, 144B in color, surface is glabrous and dull.

Inflorescence description:

*Inflorescence type.*—Terminal verticillaster, individual flowers are in whorls of 2.

*Lastingness of inflorescence.*—Approximately 5 days.

*Inflorescence size.*—An average of 13.7 cm in height and 4.6 cm in width.

*Flower type.*—Labiate.

*Flower number.*—An average of 22 per vertillicaster (11 pairs).

*Flower fragrance.*—Sage scented.

*Flower buds.*—Obovate in shape, about 1.3 cm in length and 4 mm in diameter, color (when opening); middle to the tip 199B, base 146C, petal portion 31B.

*Flower size.*—An average of 3.2 cm in depth and about 1.8 cm in width (horizontal) and 1.9 cm in height (vertical).

*Peduncle.*—An average of 13.1 cm in length and 1.5 mm in width, held straight on top of lateral branch, strong in strength, color; 143B, glabrous surface.

*Pedicels.*—An average of 5 mm in length and 0.75 mm in diameter, held at an average angle of 25°, strong in strength, color; 146A with 147A at the base, glabrous surface.

*Calyx.*—Campanulate in shape, average of 1.3 cm in length, 3 mm in width (horizontal) and 8 mm in height (vertical).

*Sepals.*—3, campanulate in arrangement, narrow obovate in shape with lower 70% fused, entire margin, acute apex, cuneate base fused into tube, an average of 1.3 cm in length and 4 mm in width, surface is dull and covered with very short glandular hairs, average of 0.4 mm in length and 186C to 186D in color, color: immature upper (inner) side; 146B, striped with 147A, immature under (outer) side; upper side 199B, underside 146C, mature upper (inner) side; 146B, striped 147A, mature under (outer) side; upper side 146A to 146B, under side 144C with tips tinged N186B.

*Petals.*—2, labiate, arranged in 2 lips, lower 65% fused into tube at base, upper and lower lip surface glabrous and dull, upper lip; broad elliptic and folded in shape, entire margin, retuse apex, 3.2 cm in length and 3 mm in width, lower lip; broad spathulate in shape, entire margin with two small lateral lobes, retuse apex, 3.3 cm in width and 1.8 mm in length, tube; 1.3 cm in length and 3 mm in width, color of upper and lower lips: when opening upper (inner) side; upper and lower lip 37B to 37C, inside of tube is 36D, when opening lower (outer) side; free parts 38B to 38C, tube 37C to 37D, top of upper part of petal 31C, when fully open upper (inner) side; upper and lower lip 37B to 37C, inside of tube is 36D, when fully open lower (outer) side; upper and lower lip 38B to 38C, tube 37C to 37D, top of upper part of petal is 31C.

Reproductive organs:

*Gynoecium.*—1 pistil, an average of 3 cm in length, style is 2.8 cm in length and NN155D in color, stigma is cleft (2 parted) and 63C in color, ovary is 145D in color.

*Androcoecium.*—2 stamens, filaments are N155B flushed with N57A in color and 1.4 cm in length, anthers are dorsifixed, narrowly elliptic in shape, an average of 1.5 mm in length and 26C in color, pollen is moderate in quantity and 17A to 17B in color.

*Fruit and seed.*—None observed to date, plants have been observed to be sterile.

It is claimed:

1. A new and distinct cultivar of *Salvia* plant named 'Salmon Dance' as herein illustrated and described.

* * * * *